United States Patent
Kuramochi et al.

(10) Patent No.: US 7,479,914 B2
(45) Date of Patent: Jan. 20, 2009

(54) A-D CONVERTER AND A-D CONVERT METHOD

(75) Inventors: Yasuhide Kuramochi, Tokyo (JP); Akira Matsuzawa, Tokyo (JP)

(73) Assignees: Advantest Corporation, Tokyo (JP); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 11/853,836

(22) Filed: Sep. 12, 2007

(65) Prior Publication Data

US 2008/0068245 A1 Mar. 20, 2008

Related U.S. Application Data

(63) Continuation-in-part of application No. 11/520,436, filed on Sep. 13, 2006.

(51) Int. Cl.
*H03M 1/12* (2006.01)
(52) U.S. Cl. .................... 341/156; 341/155; 341/159
(58) Field of Classification Search ............. 341/156, 341/159
See application file for complete search history.

(56) References Cited

U.S. PATENT DOCUMENTS

| | | | | | |
|---|---|---|---|---|---|
| 4,903,028 | A | * | 2/1990 | Fukushima | 341/156 |
| 5,187,483 | A | * | 2/1993 | Yonemaru | 341/156 |
| 5,223,836 | A | * | 6/1993 | Komatsu | 341/156 |
| 5,463,395 | A | * | 10/1995 | Sawai | 341/156 |
| 5,581,255 | A | * | 12/1996 | Hsu | 341/156 |
| 6,107,949 | A | * | 8/2000 | Gross, Jr. | 341/159 |
| 6,177,899 | B1 | * | 1/2001 | Hsu | 341/156 |
| 6,801,150 | B2 | | 10/2004 | Honda | |

(Continued)

FOREIGN PATENT DOCUMENTS

JP  H02-104024  4/1990

(Continued)

OTHER PUBLICATIONS

Article titled "An All-MOS Charge-Redistribution A/D Conversion Technique" jointly authored by Suarez et al., in IEEE International Solid-State Circuits Conference, Feb. 15, 1974 (pp. 194, 195,248).

(Continued)

*Primary Examiner*—Khai M Nguyen
(74) *Attorney, Agent, or Firm*—Jianq Chyun IP Office

(57) ABSTRACT

An A-D converter includes a plurality of comparators, each of which compares an analog input signal to analog threshold values; an upper field determination section which, during an upper determination phase, supplies in parallel to each of the plurality of comparators the plurality of analog threshold values expressing boundaries of ranges corresponding to each data value acquired from the upper field of a number of bits previously designated in the digital output signal, detects whether the analog input signal is associated with one of the ranges based on comparison results by the plurality of comparators, and narrows data values of the upper field to data values corresponding to a range between the largest analog threshold value less than or equal to the analog input signal and the smallest analog threshold value greater than or equal to the analog input signal; and a lower field determination section which, during the lower determination phase, determines values of conversion target bits based on a plurality of comparison results of the plurality of comparators.

8 Claims, 11 Drawing Sheets

U.S. PATENT DOCUMENTS

2003/0174082 A1    9/2003   Honda
2004/0189504 A1*   9/2004   Dasgupta ................ 341/156

FOREIGN PATENT DOCUMENTS

| JP | H02-278918 | 11/1990 |
| JP | 04-255113 | 9/1992 |
| JP | 05-152960 | 6/1993 |
| JP | 05-160727 | 6/1993 |
| JP | 2003-273735 | 9/2003 |
| WO | 9904496 | 1/1999 |

OTHER PUBLICATIONS

Article titled "A High-Speed, All-MOS Successive-Approximation Weighted Capacitor A/D Conversion Technique" jointly authored by McCreary et al., in IEEE International Solid-State Circuits Conference, Feb. 12, 1975 (pp. 38,39,211).

Article titled "All-MOS Charge Redistribution Analog-to-Digital Conversion Techniques-Part I" jointly authored by McCreary et al., in IEEE Journal of Solid-State Circuits, vol. SC-10, No. 6, Dec. 1975 (pp. 371-379).

* cited by examiner

A-D CONVERTER AND A-D CONVERT METHOD

CROSS REFERENCE TO RELATED APPLICATION

This is a continuation in-part application of Ser. No. 11/520,436 filed on Sep. 13, 2006, the contents of which are incorporated herein by reference.

BACKGROUND

1. Technical Field

The present invention relates to an A-D converter and an A-D convert method, and particularly relates to an A-D converter outputting a digital output signal, which is a digitalized analogue input signal, and an A-D convert method.

2. Related Art

An A-D converter converts an analogue signal into a digital signal. A-D converters are separated into two types, a single-bit type in which an analogue signal is quantized by a unit of one bit in one clock cycle and a multi-bit type in which an analogue signal is quantized by a unit of plural bits in one clock cycle. As an example of a single bit format A-D converter, a successive approximation type A-D converter (see, e.g., Ricardo E. Suarez, Paul R. Gray and David A. Hodges, "An All-MOS Charge-Redistribution A/D Conversion Technique", IEEE International Solid-State Circuits Conference, 1974, P. 194-195,248, James McCreary and Paul R. Gray, "A High-Speed, All-MOS Successive-Approximation Weighted Capacitor A/D Conversion Technique", IEEE International Solid-State Circuits Conference, 1975, P. 38-39,211, JAMES L. McCREARY and PAUL R. GRAY, "All-MOS Charge Redistribution Analog-to-Digital Conversion Techniques—Part 1", IEEE JOURNAL OF SOLID-STATE CIRCUITS, VOL.SC-10, NO. 6, December 1975, P. 371-379) and a delta sigma type A-D converter are known. As a multi-bit A-D converter, a flash A-D converter, for example, is known.

The multi-bit A-D converter has a relatively short conversion time compared to the single bit A-D converter. However, in a case where the multi-bit A-D converter has high resolution, circuit size thereof becomes large. On the other hand, the circuit size of the single bit A-D converter is relatively small compared to that of the multi-bit A-D converter. However, in a case where the single bit A-D converter has a certain resolution, the conversion time becomes long because one bit at a time is converted.

Furthermore, in a case where high resolution is realized, both the multi-bit A-D converter and the single bit A-D converter experience decreased precision because a quantization range is narrowed, thereby causing a decrease in an acceptable amount of signal noise. In a case where the input signal is amplified by an operational amplifier in an attempt to solve the aforementioned problem, the multi-bit A-D converter and the single bit A-D converter consume an increased amount of power, and furthermore, the precision relies on characteristics of the operational amplifier.

SUMMARY

Therefore, it is an object of an aspect of the present invention to provide an A-D converter and an A-D convert method, which is capable of overcoming the above drawbacks accompanying the related art. The above and other objects can be achieved by combinations described in the independent claims. The dependent claims define further advantageous and exemplary combinations of the present invention.

According to a first aspect related to the innovations herein, an A-D converter outputting a digital output signal which is a digitalized analog input signal is provided. The A-D converter according to the first aspect includes a plurality of comparators, each of which compares the analog input signal to analog threshold values; a upper field determination section which, during an upper determination phase, supplies in parallel to each of the plurality of comparators the plurality of analog threshold values expressing boundaries of ranges corresponding to each data value acquired from the upper field of a number of bits previously designated in the digital output signal, detects whether the analog input signal is associated with one of the ranges based on comparison results by the plurality of comparators, and narrows down data values of the upper field to data values corresponding to a range between the largest analog threshold value less than or equal to the analog input signal and the smallest analog threshold value greater than or equal to the analog input signal; a bit selection section which, during a lower determination phase, selects conversion target bits sequentially from a highest bit to a lowest bit within a lower field while ignoring the upper field in the digital output signal; a threshold control section which, during the lower determination phase, determines threshold data values expressing boundary values of zero and one of the conversion target bits based on a predetermined value of a bit higher than the conversion target bits; a D-A conversion section which, during the lower determination phase, supplies to each of the plurality of comparators the analog threshold values which are the D-A converted threshold data; and a lower field determination section which, during the lower determination phase, determines values of the conversion target bits based on a plurality of comparison results of the plurality of comparators.

According to a second aspect related to the innovations herein, an A-D conversion method performed by an A-D converter outputting a digital output signal which is a digitalized analog input signal, in which the A-D converter includes a plurality of comparators, each of which compares the analog input signal to analog threshold values, is provided. The A-D conversion method includes the steps of, during an upper determination phase, supplying in parallel to each of the plurality of comparators the plurality of analog threshold values expressing boundaries of ranges corresponding to each data value acquired from the upper field of a number of bits previously designated in the digital output signal, detecting whether the analog input signal is associated with one of the ranges based on comparison results by the plurality of comparators, and narrowing down data values of the upper field to data values corresponding to a range between the largest analog threshold value less than or equal to the analog input signal and the smallest analog threshold value greater than or equal to the analog input signal; during a lower determination phase, selecting conversion target bits sequentially from a highest bit to a lowest bit within a lower field while ignoring the upper field in the digital output signal; during the lower determination phase, determining threshold data values expressing boundary values of zero and one of the conversion target bits based on a predetermined value of a bit higher than the conversion target bits; during the lower determination phase, supplying to each of the plurality of comparators the analog threshold values which are the D-A converted threshold data; and during the lower determination phase, determining values of the conversion target bits based on a plurality of comparison results of the plurality of comparators.

The summary clause does not necessarily describe all necessary features of the embodiments of the present invention.

The present invention may also be a sub-combination of the features described above. The above and other features and advantages of the present invention will become more apparent from the following description of the embodiments taken in conjunction with the accompanying drawings.

DESCRIPTION OF EXEMPLARY EMBODIMENTS

Hereinafter, an aspect of the present invention will be described based on an embodiment. The embodiment does not limit the invention according to the claims, and all the combinations of the features described in the embodiment are not necessarily essential to means provided by aspects of the invention.

Figure 1:
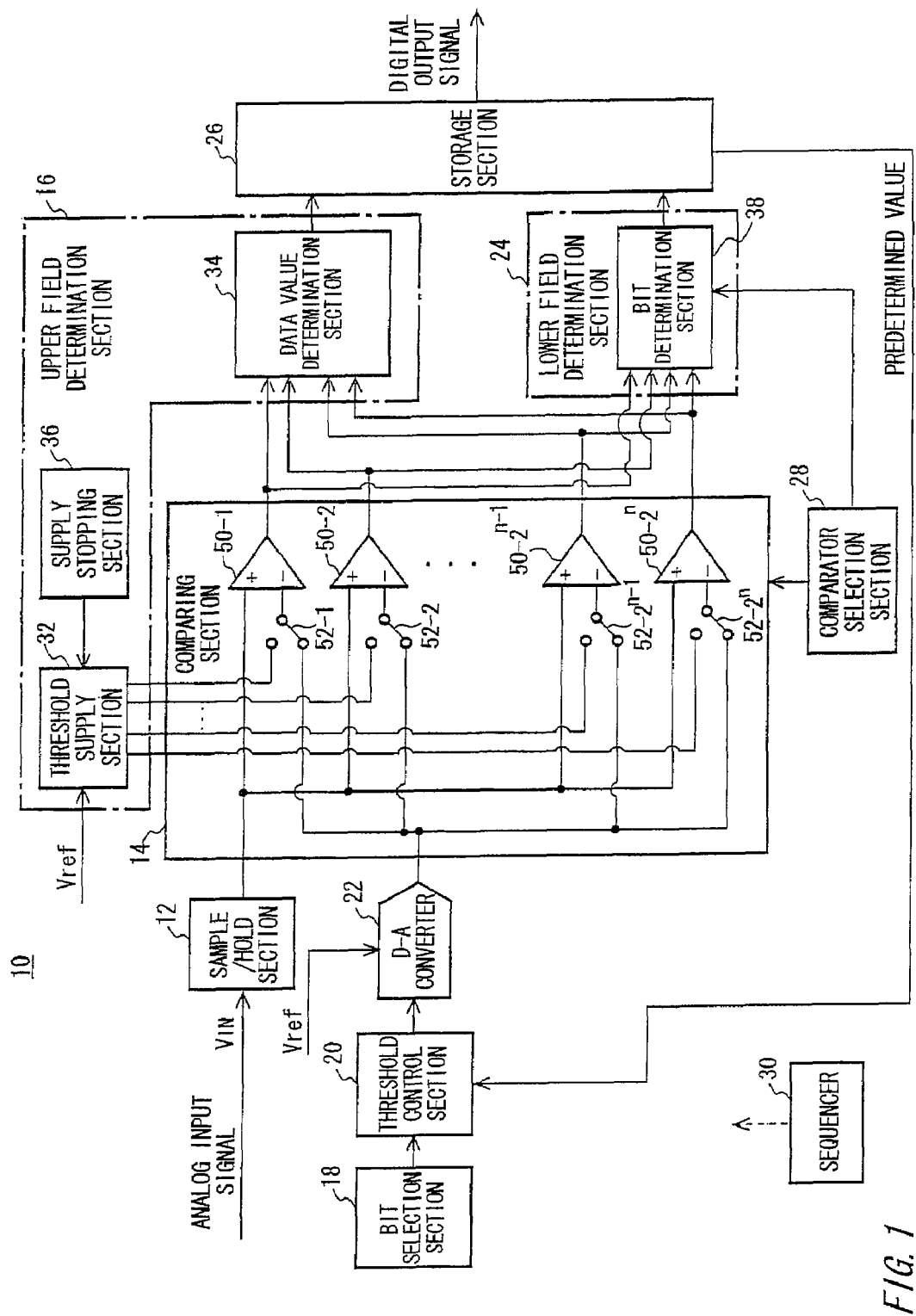
FIG. 1 shows a structure of an A-D (Analog to Digital) converter 10 according to an embodiment of the present invention.

FIG. 1 shows a structure of an A-D (Analog to Digital) converter 10 according to an embodiment of the present invention. The A-D converter 10 outputs a digital output signal, which is a digitalized analog input signal. In the present embodiment, the A-D converter 10 converts a voltage value $V_{IN}$ of the analog input signal into an m-bit digital output signal for every prescribed conversion cycle (A-D conversion cycle). Here, m is an integer greater than or equal to two.

Furthermore, the A-D converter 10 performs a two-step conversion phase during each A-D conversion cycle. Specifically, the A-D converter 10 first performs an upper determination phase and then performs a lower determination phase during each A-D conversion cycle.

During the upper determination phase, the A-D converter 10 determines data values of an upper field of the number of bits previously determined in the digital output signal by flash converting the analog input signal. For example, the A-D converter 10 sets the upper field to be a range from a highest bit in the digital output signal (m-th bit) to a (m-n)-th bit, and the data values of this upper field may be determined during the upper determination phase. Here, n is an integer greater than or equal to one but less than m.

During the lower determination phase, the A-D converter 10 determines data values of the lower field, which includes the bits omitted from the upper field in the digital output signal, by successively approximating the analog input signal. For example, the A-D converter 10 sets the lower field to be a range from a (m-n-1)-th bit to a lowest bit (first bit) in the digital output signal, and the data values of this lower field may be determined during the lower determination phase. Here, for example, the A-D converter 10 may also set the lower field to be a range from a bit higher than an (m-n-1)-th bit to the lowest bit (first bit).

The A-D converter 10 is provided with a sample/hold unit 12, a comparing section 14, an upper field determination section 16, a bit selection section 18, a, threshold control section 20, a D-A conversion section 22, a lower field determination section 24, a storage section 26, a comparator selection section 28, and a sequencer 30. The sample/hold unit 12 samples the analog input signal and holds the sampled analog input signal. For example, the sample/hold unit 12 may sample the voltage value $V_{IN}$ of the analog input signal using a capacitor and temporarily hold the voltage value VIN.

The comparing section 14 includes a plurality of comparators 50 and a plurality of threshold value switching switches 52. In the present embodiment, the comparing section 14 includes $2^n$ comparators 50 (50-1 to 50-$2^n$) and $2^n$ threshold value switching switches 52 (52-1 to 52-$2^n$).

The plurality of comparators 50 each compare an analog input signal to an analog threshold value. For example, in a case where a comparison result is that the analog input signal is beyond the analog threshold value, the plurality of comparators 50 each output L logic (zero), and in a case where the comparison result is that the analog input signal is below the analog threshold value, the plurality of comparators 50 each output H logic (one). In the present embodiment, each of the $2^n$ comparators 50 compare the voltage value $V_{IN}$ of an analog input signal to a voltage value supplied as the analog threshold value.

The plurality of threshold value switching switches 52 are each disposed to correspond one to one with each of the plurality of comparators 50. During the upper determination phase, each of the plurality of threshold value switching switches 52 supplies to each corresponding comparator 50 the corresponding analog threshold value from among the plurality of analog threshold values output in parallel from the upper field determination section 16. During the lower determination phase, the plurality of threshold value switching switches 52 each supply to the corresponding comparator 50 the corresponding analog threshold value output from the D-A conversion section 22.

The upper field determination section 16 includes a threshold supply section 32, a data value determination section 34, and a supply stopping section 36. During the upper determination phase, the upper field determination section 16 determines the data values of the upper field in the digital output signal.

During the upper determination phase, the threshold supply section 32 supplies in parallel to each of the plurality of comparators 50 the plurality of analog threshold values expressing boundaries of a range corresponding to each data value acquired from the upper field. In the present embodiment, the threshold supply section 32 supplies in parallel to each of the $2^n$ comparators 50 $2^n$ voltage signals expressing boundaries of each voltage range in a case where the range between a reference voltage $V_{ref}$ and a ground (or the range between a positive reference voltage $V_{ref}$ and a negative reference voltage $-V_{ref}$) is divided into $2^n$ generally uniform voltage ranges. For example, the threshold supply section 32 may generate in parallel $2^n$ levels of voltage signals by separating the voltage between the reference voltage $V_{ref}$ and the ground using a plurality of resistances connected in parallel.

Each of the plurality of comparators 50 output to the data value determination section 34 the comparison result of the analog input signal and the analog threshold value output by the threshold supply section 32. The data value determination section 34, based on the input a plurality of comparison results, detects whether the analog input signal is associated with one of the ranges from among the ranges corresponding to each data value acquired from the upper filed. Then, based on the comparison results by the plurality of comparators 50, the data value determination section 34 narrows down the data values of the upper field to the data values corresponding to a range between the largest analog threshold value less than or equal to the analog input signal and the smallest analog threshold value greater than or equal to the analog input signal. Therefore, the data value determination section 34 can determine the data values of the upper field in the digital output signal.

During the upper determination phase, the supply stopping section 36 stops the supply of analog threshold values from the threshold supply section 32 to the plurality of comparators 50. Therefore, the supply stopping section 36 decreases the power consumed by the A-D converter 10.

During the lower determination phase, the bit selection section 18 selects conversion target bits sequentially from upper bits to the lower bits within the lower field. For example, during the lower determination phase, the bit selection section 18 may select the conversion target bits one at a time sequentially from the highest bit to the lowest bit within the lower field for every timing period of a sampling clock.

During the lower determination phase, the threshold control section 20 determines threshold data expressing boundary values of the conversion target bit as zero and one based on a previously determined value of a bit higher than the conversion target bit. In other words, the threshold control section 20 determines the threshold data expressing boundary values such that the value of the conversion target bit is between zero and one in the digital output signal based on a previously determined value stored in the storage section 26.

For example, in a case where the threshold control section 20 determines the values sequentially from an upper bit of the digital output signal, data values expressing intermediate values in a range acquired from a bit field having as of yet undetermined values may be set as the threshold value data. For example, suppose that the threshold control section 20 determines that the number of bits of the threshold value data and the number of bits (m bits) of the digital output signal are the same. In such a case, the threshold control section 20 outputs threshold value data in which the bits that are higher in a column corresponding to the conversion target bit are set to be the same as an already determined value, the bits of the column corresponding to the conversion target bit are set to be one, and the bits lower in a column corresponding to the conversion target bit are set to zero.

During the lower determination phase, the D-A conversion section 22 supplies to each of the plurality of comparators 50 the analog threshold values containing the threshold value data that has been D-A converted. In the present embodiment, the D-A conversion section 22 has a resolution at least equal to a number of bits (m bits) of the digital output signal and the reference potentials are set to be the reference voltage $V_{ref}$ and the ground (or the reference voltage $V_{ref}$ and the negative reference voltage $-V_{ref}$). Therefore, by D-A converting the threshold value data represented by m bits, the D-A conversion section 22 can output the analog threshold values congruent with the boundaries of the range corresponding to the data values acquired from the digital output signal.

The lower field determination section 24 includes a bit determination unit 38. During the lower determination phase, the plurality of comparators 50 output to the bit determination unit 38 the comparison result of the analog input signal and the analog threshold value output by the D-A conversion section 22. Then, based on the plurality of comparison results by the by the plurality of comparators 50, the bit determination unit 38 determines the value (zero or one) of the conversion target bits. For example, the bit determination unit 38 may make a determination based on a majority of the plurality of comparison results and determine the conversion target bit values to be zero or one. In the present embodiment, the bit determination unit 38 determines the conversion target bit values based on the comparison results of the k (k being an integer greater than or equal to two and less than or equal to 2n) comparators 50 selected by the comparator selection section 28 from among the $2^n$ comparators 50 included in the comparing section 14.

The storage section 26 stores the data values of the upper and lower fields of the digital output signal determined by the upper field determination section 16 and the lower field determination section 24. For example, the storage section 26 may sequentially output the data values of the digital output signal determined for every A-D conversion cycle.

The comparator selection section 28 selects the comparators 50, from among the plurality of comparators 50 included in the comparing section 14, to be used by the bit determination unit 38 to determine the conversion target bit values. In the present embodiment, the comparator selection section 28 selects the k comparators 50 having small margins of error from among the $2^n$ comparators 50.

For example, the comparator selection section 28 measures a margin of error for each of the $2^n$ comparators 50 included in the comparing section 14 by connecting a reference potential to an input terminal of a comparator 50, changing the potential of another input terminal, and measuring a difference between the reference potential and the potential reflecting the comparison result. The comparator selection section 28 may then select the k comparators 50 having small margins of error from among the $2^n$ comparators 50 based on the measurement result. Furthermore, in a case where the margin of error for each of the $2^n$ comparators 50 is measured in advance, such as when shipped from a factory, the specific information concerning the comparators 50 having small margins of error may be stored in the comparator selection section 28 in advance, so that the comparator selection section 28 may select the k comparators 50 based on this stored information.

The sequencer 30 controls overall performance of the A-D converter 10. For example, the sequencer 30 controls timing of the performances of the upper determination phase and lower determination phase, output of a sample/hold signal designating sample timing and hold timing of the analog input signal, output timing of the digital output signal stored in the storage section 26, and the like.

Figure 2:
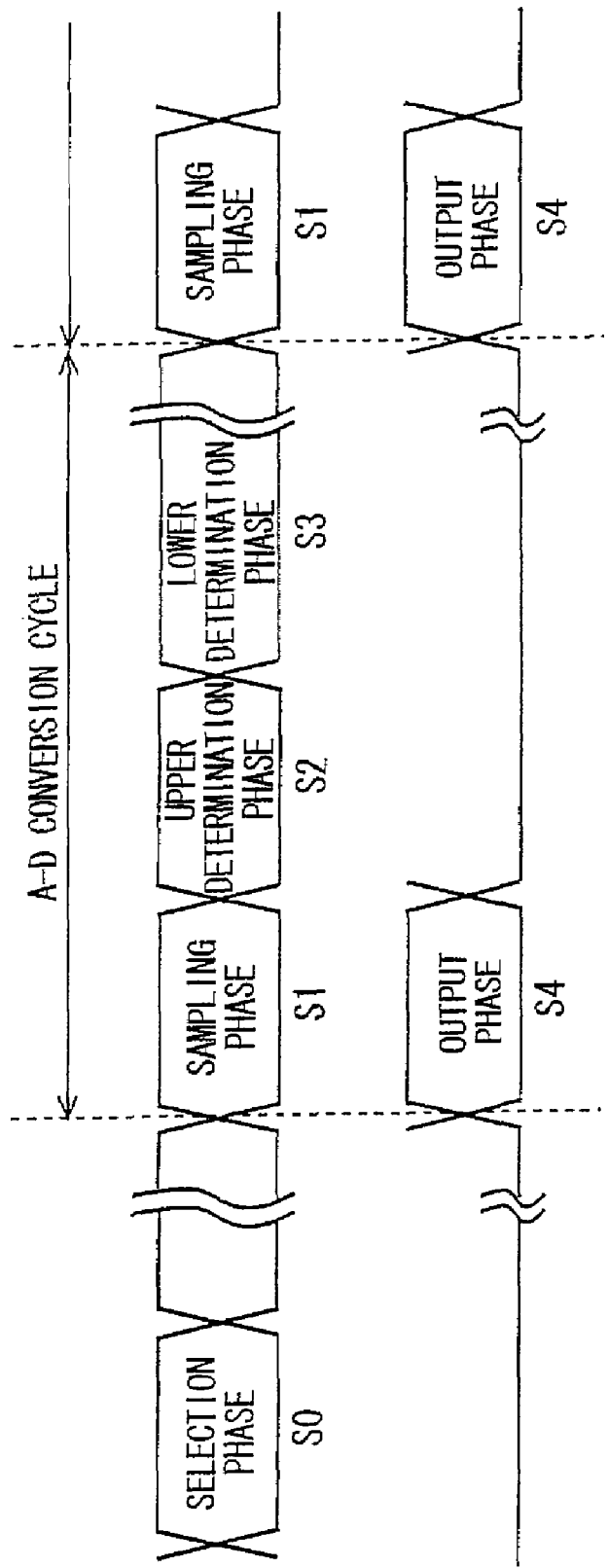
FIG. 2 shows each phase of an analog to digital conversion process by the A-D converter 10 according to an embodiment of the present invention.

FIG. 2 shows each phase of an analog to digital conversion process by the A-D converter 10 according to the present embodiment. First, prior to the A-D conversion process, the A-D converter 10 performs a selection phase (S0). During the selection phase (S0), the A-D converter 10 selects the k comparators 50 having small margins of error.

Upon initiation of the A-D conversion process, the A-D converter 10, during a sampling phase (S1), samples the analog input signal. The A-D converter 10 then holds the sampled analog input signal until completion of the lower determination phase (S3).

Next, during the upper determination phase (S2), the A-D converter 10 determines the data values corresponding to the upper field of the digital output signal. Then, during the lower determination phase (S3), the A-D converter 10 determines the data values corresponding to the lower field of the digital output signal. Next, during an output phase (S4), the A-D converter 10 outputs the data values of all the fields of the digital output signal determined during the upper determination phase (S2) and the lower determination phase (S3).

The A-D converter 10 repeats the aforementioned phases S1 to S4 for every A-D conversion cycle. Therefore, the A-D converter 10 can output one sample of data values, which represent the analog input signal converted to a digital value, for every A-D conversion cycle. Furthermore, where the A-D converter 10 performs the sampling phase (S1), the upper determination phase (S2), and the lower determination phase (S3) for a single A-D conversion cycle, the output phase (S4) for outputting the data values determined during this single A-D conversion cycle may be executed after this A-D conversion cycle is finished.

Figure 3:
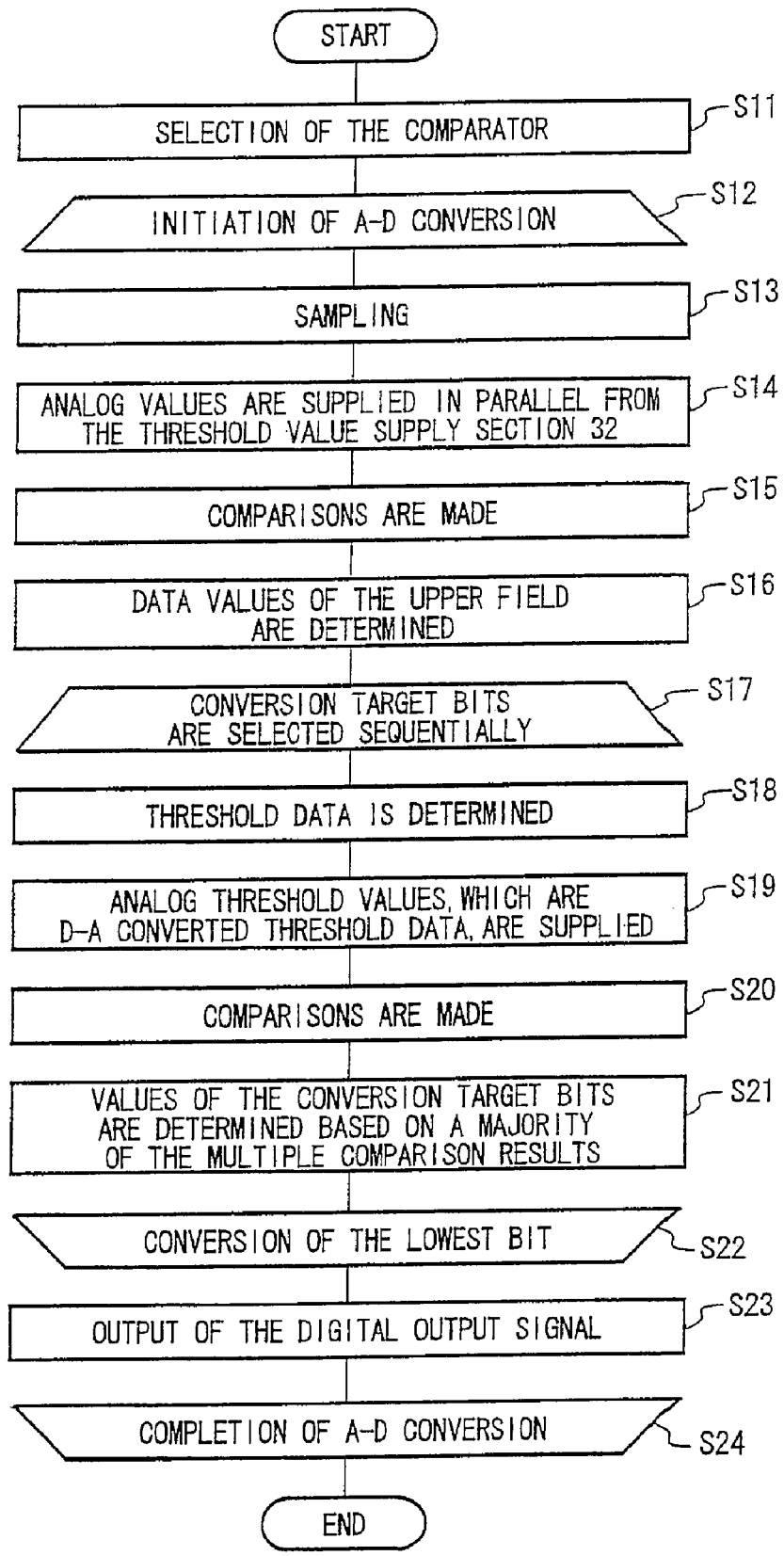
FIG. 3 shows a flow of the analog to digital conversion process by the A-D converter 10 according to an embodiment of the present invention.
Figure 4:
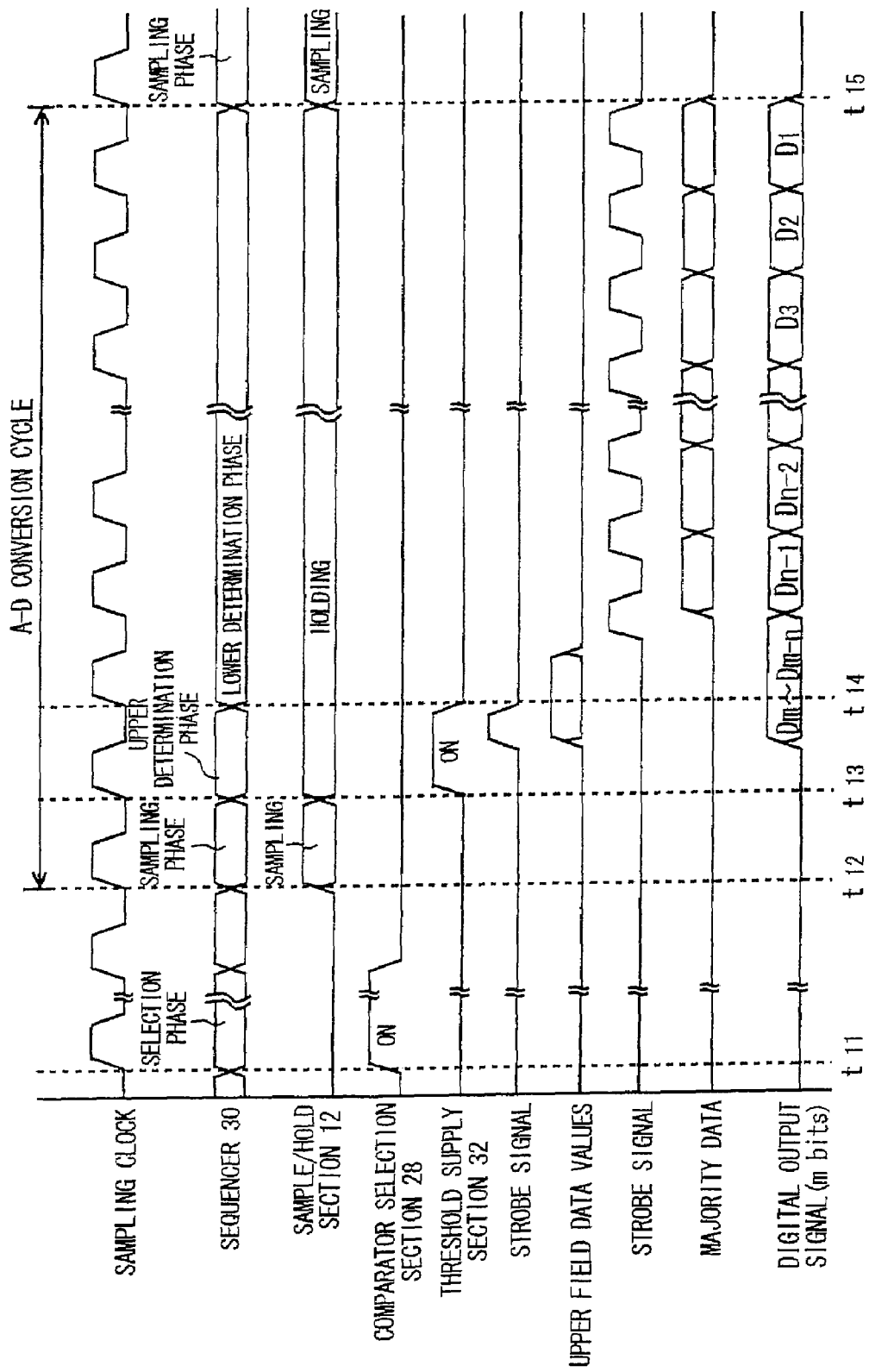
FIG. 4 shows an example timing chart of the analog to digital conversion process by the A-D converter 10 according to an embodiment of the present invention.

FIG. 3 shows a flow of the analog to digital conversion process by the A-D converter 10 according to the present embodiment. FIG. 4 shows an example timing chart of the analog to digital conversion process by the A-D converter 10 according to the present embodiment.

First, during checking or the like of the A-D converter 10, the sequencer 30 operates the comparator selection section 28 (S11, t11 to t12). The comparator selection section 28, under control of the sequencer 30, selects the k comparators 50 having small margins of error from among the $2^n$ comparators 50 of the comparing section 14. The process performed at step S11 corresponds to the selection phase (S0) process of shown in FIG. 2.

Next, upon initiation of the A-D conversion process, the sequencer 30 repeatedly performs the processes from step S13 to step S23 (S12, S24, t12 to t15) for every A-D conversion cycle.

In each A-D conversion cycle, the sequencer 30 first instructs the sample/hold unit 12 to perform sampling (S13, t12) by controlling the sample/hold signal. Upon receiving sampling instruction from the sequencer 30, the sample/hold unit 12 samples the analog input signal (t12 to t13). The sequencer 30 instructs the sample/hold unit 12 to hold at a time when the sampling is completed (t13). Upon receiving hold instruction from the sequencer 30, the sample/hold unit 12 holds the sampled analog input signal (t13 to t15). The sequencer 30 continues the hold instruction until the A-D conversion cycle is finished (t15). The process at step S13 corresponds to the sampling phase (S1) process shown in FIG. 2.

Next, the sequencer 30 controls the $2^n$ threshold value switching switches 52 to supply in parallel to the corresponding comparators 50 each of the analog threshold values of $2^n$ levels generated from the threshold supply section 32 (S14, t13 to t14). The sequencer 30 then supplies to each of the $2^n$ comparators 50 a strobe signal designating comparison timing (S15, t13 to t14). Each of the $2^n$ comparators 50, with a timing designated by the strobe signals, compares the analog input signal held by the sample/hold unit 12 to the analog threshold value supplied from the threshold supply section 32.

Next, the data value determination section 34 determines the data values of the upper field (S16, t14) based on the comparison results of the plurality of comparators 50. Specifically, the data value determination section 34 determines the data values of the upper field, which are the data values corresponding to the range between the largest analog threshold value less than or equal to the analog input signal and the smallest analog threshold value greater than or equal to the analog input signal. The process at steps S14 to S16 corresponds to the upper determination phase (S2) process shown in FIG. 2.

Next, the sequencer 30 operates the bit selection section 18. Upon receiving performance initiation instruction from the sequencer 30, the bit selection section 18 synchronizes with the sampling clock and sequentially selects the conversion target bits one at a time from the highest bit to the lowest bit within the lower field (S17, S22, t14 to t15). During selection of each conversion target bit, the bit selection section 18 performs the processes from step S18 to step S21.

During selection of each conversion target bit, the threshold control section 20 determines the threshold value data expressing the boundary values of zero and one of the conversion target bits based on predetermined values of bits higher than the conversion target bits (S18). Next, the D-A conversion section 22 commonly supplies to each of the $2^n$ comparators 50 the analog threshold values, which are the D-A converted threshold value data (S19). For example, the D-A conversion section 22 may at least supply the analog threshold values to the k comparators 50 selected at step S11.

Next, the sequencer 30 supplies the strobe signals to each of the $2^n$ comparators 50 (S20, t14 to t15). For example, the sequencer 30 may supply the strobe signals to the k comparators 50 selected at step S11. Each of the $2^n$ comparators 50, with a timing designated by strobe signals, compares the analog input signal held by the sample/hold unit 12 to the analog threshold value supplied from the D-A conversion section 22. Next, the bit determination unit 38 determines the conversion target bit values (zero or one) by making a determination based on a majority of the comparison results of the k comparators 50 selected at step S11 (S21).

As a result of the processes of steps S18 to S21 concerning each bit from the highest bit to the lowest bit within the lower field, the lower field determination section 24 can determine the data values of the lower field. The processes at steps S17 to S22 correspond to the lower determination phase (S3) shown in FIG. 2.

Next, after the data values of the lower field are determined (for example, in the next A-D conversion cycle), the sequencer 30 instructs the storage section 26 to output the digital output signal (S23). Upon receiving output instruction from the sequencer 30, the storage section 26 outputs a one-sample unit of data values of all the fields of the digital output signal determined at step S16 and step S21. The process at step S23 corresponds to the output phase (S4) process shown in FIG. 2. Then, by repeating the aforementioned processes of steps S13 to S23, the A-D converter 10 can output over time the digital output signal corresponding to the analog input signal.

The A-D converter 10 described above determines the data values of the upper field using flash conversion with a short conversion time and determines the data values of the lower field using successive conversion that has a high resolution and a simple configuration. Therefore, through the A-D converter 10, A-D conversion with short conversion time and high resolution can be realized.

Furthermore, with regards to a quantization range being narrowed to-result in a decrease in the acceptable amount of signal noise in the lower field, the A-D converter uses the plurality of comparators 50 to compare in parallel the analog input signal and the analog threshold values to determine the value of each bit by, for example, making a determination based on a majority of the plurality of comparison results. Therefore, through the A-D converter 10, precise A-D conversion can be achieved. Furthermore, through the A-D converter 10, even more precise A-D conversion of the lower field can be achieved by using the comparison results of the comparators 50 having small margins of error selected by the comparator selection section 28.

During the lower determination phase, the A-D converter 10 may make the conversion time of a prescribed bit longer than the conversion time of bits higher than the prescribed bit. For example, the A-D converter 10 may make the conversion time of the lowest bit double the conversion time of the highest bit in the lower field. Therefore, through the A-D converter 10, the value of lower bits that have a decreased acceptable amount of signal noise can be precisely A-D converted.

Figure 5:
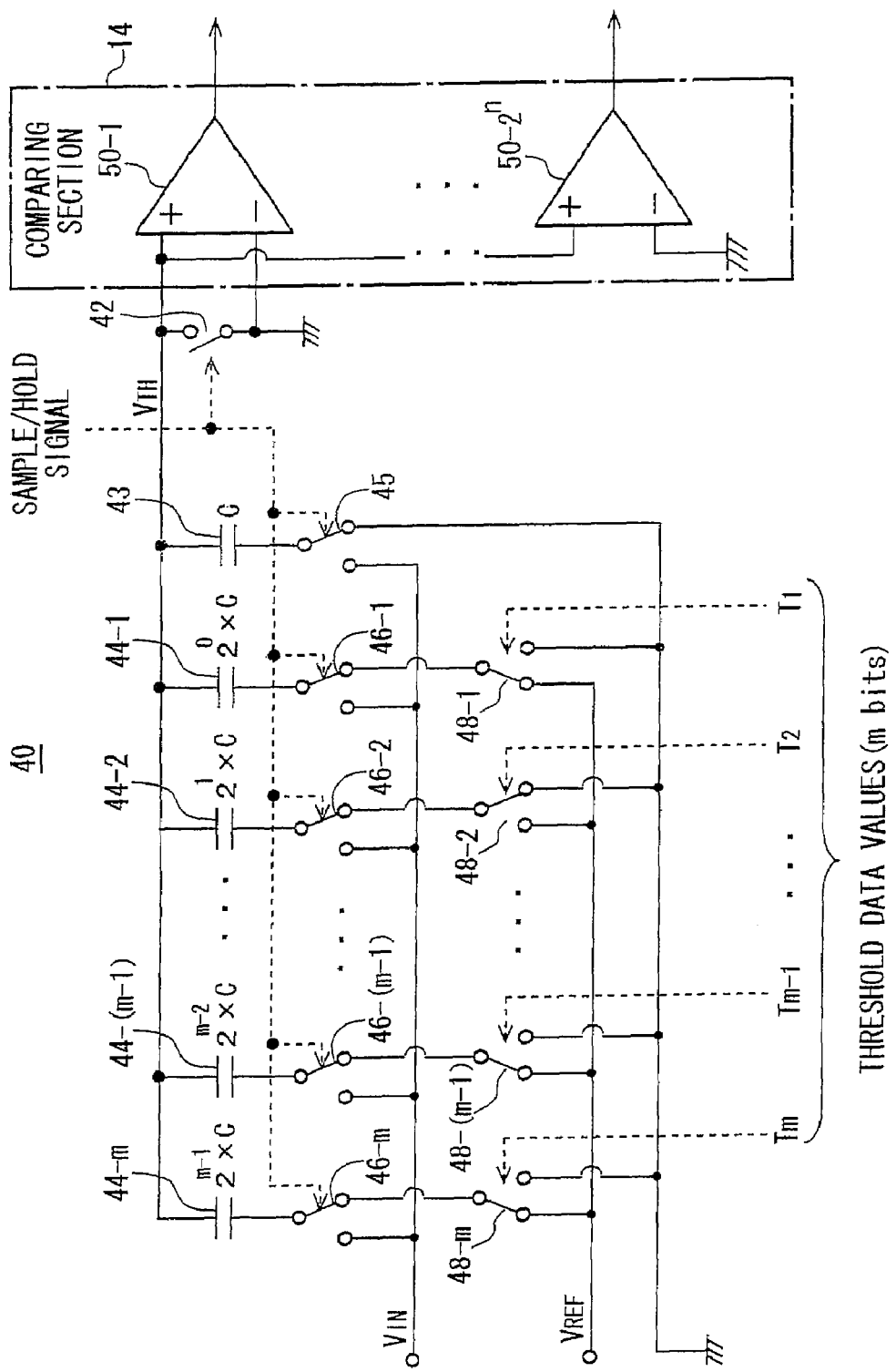
FIG. 5 shows a structure of a charge redistribution type D-A converter 40 together with a comparing section 14 according to a first aspect of an embodiment of the present invention.

FIG. 5 shows a structure of a charge redistribution type D-A converter 40 together with the comparing section 14 according to a first aspect of the present embodiment. The A-D converter 10 according to the first aspect adopts generally the same structure and function as the A-D converter 10 according to the present embodiment shown in FIG. 1, and therefore the following description omits identical points.

The A-D converter 10 according to the first aspect is provided with the charge redistribution type D-A converter 40 shown in FIG. 5 in addition to the sample/hold unit 12 and the D-A conversion section 22 shown in FIG. 1. The charge redistribution type D-A converter 40 includes the function of the sample/hold unit 12 and the function of the D-A conversion section 22.

In the first aspect, a minus input terminal of each of the plurality of comparators 50 is connected to a ground. In a case where a voltage applied to a plus input terminal of each of the comparators 50 is greater than or equal to a voltage applied to the minus input terminal (ground potential), an H logic (one) is output. In a case where the voltage applied to the plus input terminal less than the voltage applied to the minus input terminal (ground potential), an L logic (zero) is output.

The charge redistribution type D-A converter 40 includes a sampling switch 42, an adjustment capacitor 43, first to m-th capacitors 44-1 to 44-$m$, an adjustment switch 45, first to m-th input switching switches 46-1 to 46-$m$, and first to m-th bit switches 48-1 to 48-$m$. Here, in FIG. 5, m is a number of bits (an integer greater than or equal to two) of the threshold value data.

In a case where sampling is designated by the sample/hold signal, the sampling switch 42 connects the plus terminal of each comparator 50 to the ground. In a case where holding is designated by the sample/hold signal, the sampling switch 42 opens a space between the plus terminal of each comparator 50 and the ground.

The adjustment capacitor 43 has a capacity of a prescribed value C. One end of the adjustment capacitor 43 is connected to the plus terminal of each comparator 50.

The first to m-th capacitors 44-1 to 44-$m$ correspond sequentially to each bit of the threshold value data of m bits. In other words, the first capacitor 44-1 corresponds to the first bit from the bottom (the lowest bit), the second capacitor 44-2 corresponds to the second bit from the bottom, the third capacitor 44-3 corresponds to the third bit from the bottom, . . . , and the m-th capacitor 44-$m$ corresponds to the m-th bit from the lowest bit (the highest bit). The capacity of the first capacitor 44-1 is set to be $2^0 \times C$, which is $2^0$ times (1 time) the prescribed value C, the capacity of the second capacitor 44-2 is set to be $2^1 \times C$, which is $2^1$ times the prescribed value C, the capacity of the third capacitor 44-3 is set to be $2^2 \times C$, which is $2^2$ times the prescribed value C, . . . , the capacity of the m-th capacitor 44-$m$ is set to be $2^{m-1} \times C$, which is $2^{m-1}$ times the prescribed value C. An end of each first to m-th capacitor 44-1 to 44-$m$ is connected to the plus input terminal of each comparator 50.

In a case where sampling is designated by the sample/hold signal, the adjustment switch 45 applies the analog input voltage $V_{IN}$ to a terminal on a side that is not connected to the plus input terminal of each comparator 50 in the adjustment capacitor 43 (hereinafter this terminal is referred to as the "other terminal" of the adjustment capacitor 43). In a case where holding is designated by the sample/hold signal, the adjustment switch 45 applies a ground potential to the other terminal of the adjustment capacitor 43.

The first to m-th input switching switches 46-1 to 46-$m$ correspond to the first to m-th capacitors 44-1 to 44-$m$, respectively. In a case where sampling is designated by the sample/hold signal, the first to m-th input switching switches 46-1 to 46-$m$ apply the analog input voltage $V_{IN}$ to the terminal on the side that is not connected to the plus input terminal of each comparator 50 in the first to m-th capacitors 44-1 to 44-$m$ (hereinafter this terminal is referred to as "the other terminal" of the first to m-th capacitors 44-1 to 44-$m$). In a case where holding is designated by the sample/hold signal, the first to m-th input switching switches 46-1 to 46-$m$ apply a reference signal $V_{REF}$ and the ground potential to the other terminals of the first to m-th capacitors 44-1 to 44-$m$.

The first to m-th bit switches 48-1 to 48-$m$ correspond sequentially to each bit of the threshold value data of m bits. In other words, the first bit switch 48-1 corresponds to the first bit from the bottom (the lowest bit), the second bit switch 48-2 corresponds to the second bit from the bottom, the third bit switch 48-3 corresponds to the third bit from the bottom, . . . , and the m-th bit switch 48-$m$ corresponds to the m-th bit from the lowest bit (the highest bit). In a case where the bit values corresponding to the threshold value data are H logic (one), each of the first to m-th bit switches 48-1 to 48-$m$ apply the reference signal $V_{REF}$ to the other terminal of each of the corresponding first to m-th capacitors 44-1 to 44-$m$, respectively. In a case where the bit values corresponding to the threshold value data are of L logic (zero), each of the first to m-th bit switches 48-1 to 48-$m$ apply the ground potential to the other terminal of each of the corresponding first to m-th capacitors 44-1 to 44-$m$, respectively.

During sampling, the charge redistribution type D-A converter 40 having such a configuration connects an end of the adjustment capacitor 43 and each of the first to m-th capacitors 44-1 to 44-$m$ to the ground and applies the voltage value $V_{IN}$ of the analog input signal to the other terminals thereof. Accordingly, during sampling, the adjustment capacitor 43 and the first to m-th capacitors 44-1 to 44-$m$ can sample the voltage value $V_{IN}$ of the analog input signal.

Furthermore, during holding, the charge redistribution type D-A converter 40 having such a configuration disconnects the end of the adjustment capacitor 43 from the ground and stops the application of the voltage value $V_{IN}$ of the analog input signal to the other terminal of the adjustment capacitor 43. Accordingly, during holding, the adjustment capacitor 43 applies an inverse voltage ($-V_{IN}$) of the voltage $V_{IN}$ of the held analog input signal to the plus input terminal of each comparator 50.

In addition, during holding, the charge redistribution type D-A converter 40 having such a configuration disconnects the ends of the first to m-th capacitors 44-1 to 44-m from the ground. Furthermore, during holding, each of the first to m-th capacitors 44-1 to 44-m apply the voltage $V_{REF}$ to the other terminal in a case where the bit values corresponding to the threshold value data are of H logic (one) and apply the ground potential to the other terminal in a case where the bit values corresponding to the threshold value data are of L logic (zero).

Accordingly, during holding, the adjustment capacitor 43 and the first to m-th capacitors 44-1 to 44-m can each apply a voltage $V_{TH}$, shown below in Equation (1), to the plus input terminal of each of the comparators 50.

$$V_{TH} = -V_{IN} + \{(V_{REF}/2^1) \times (T_m) + (V_{REF}/2^2) \times (T_{m-1}) + \ldots + (V_{REF}/2^{m-1}) \times (T_2) + (V_{REF}/2^m) \times (T_1)\} \quad \text{Equation (1):}$$

In Equation (1), $T_1$ represents the logic value of the first bit from the bottom (the lowest bit) of the threshold value data, $T_2$ represents the logic value of the second bit from the bottom of the threshold value data, ..., $T_m$ represents the logic value of the m-th bit from the bottom (the highest bit) of the threshold value data.

The voltage $V_{TH}$ shown in Equation (1) becomes greater than or equal to the ground potential (0V) if the voltage value $V_{IN}$ of the analog input signal is greater than or equal to the threshold value voltage corresponding to the threshold data (the voltage expressed in Equation 1 within the parentheses { }). On the other hand, the voltage $V_{TH}$ becomes less than the ground potential (0V) if the voltage value $V_{IN}$ of the analog input signal is less than the threshold value voltage corresponding to the threshold data.

Each of the comparators 50 then output the logic value representing the comparison result of the voltage $V_{TH}$ and the voltage value $V_{IN}$ of the analog input signal. In other words, L logic (zero) is output in a case where the voltage $V_{TH}$ of Equation (1) is greater than or equal to the ground potential and H logic (one) is output in a case where the voltage $V_{TH}$ of Equation 1 is less than the ground potential.

Through the charge redistribution type D-A converter 40 having such a configuration, a comparison between the voltage value $V_{IN}$ of the analog input signal and the voltage value corresponding to the threshold value data can be made by each comparator 50. Furthermore, through the charge redistribution type D-A converter 40 having such a configuration, the sample/hold function for the reference voltage $V_{IN}$ of the analog input signal can also be included. Therefore, the A-D converter 10 according to the first aspect need not be provided with the sample/hold unit 12, thereby achieving a simpler configuration.

Furthermore, in a case where sampling is performed with the same capacity as in a case where the sample/hold unit 12 is provided, the A-D converter 10 according to the first aspect can shorten the sampling time because the capacity of each individual capacitor 44 is decreased, thereby decreasing a time constant. Furthermore, in a case where sampling of the analog input signal is performed where with each individual capacitor 44 having the same precision as the sample/hold unit 12, the A-D converter 10 according to the first aspect can perform A-D conversion with high precision because noise included in the plurality of capacitors 44 can be averaged.

Figure 6:
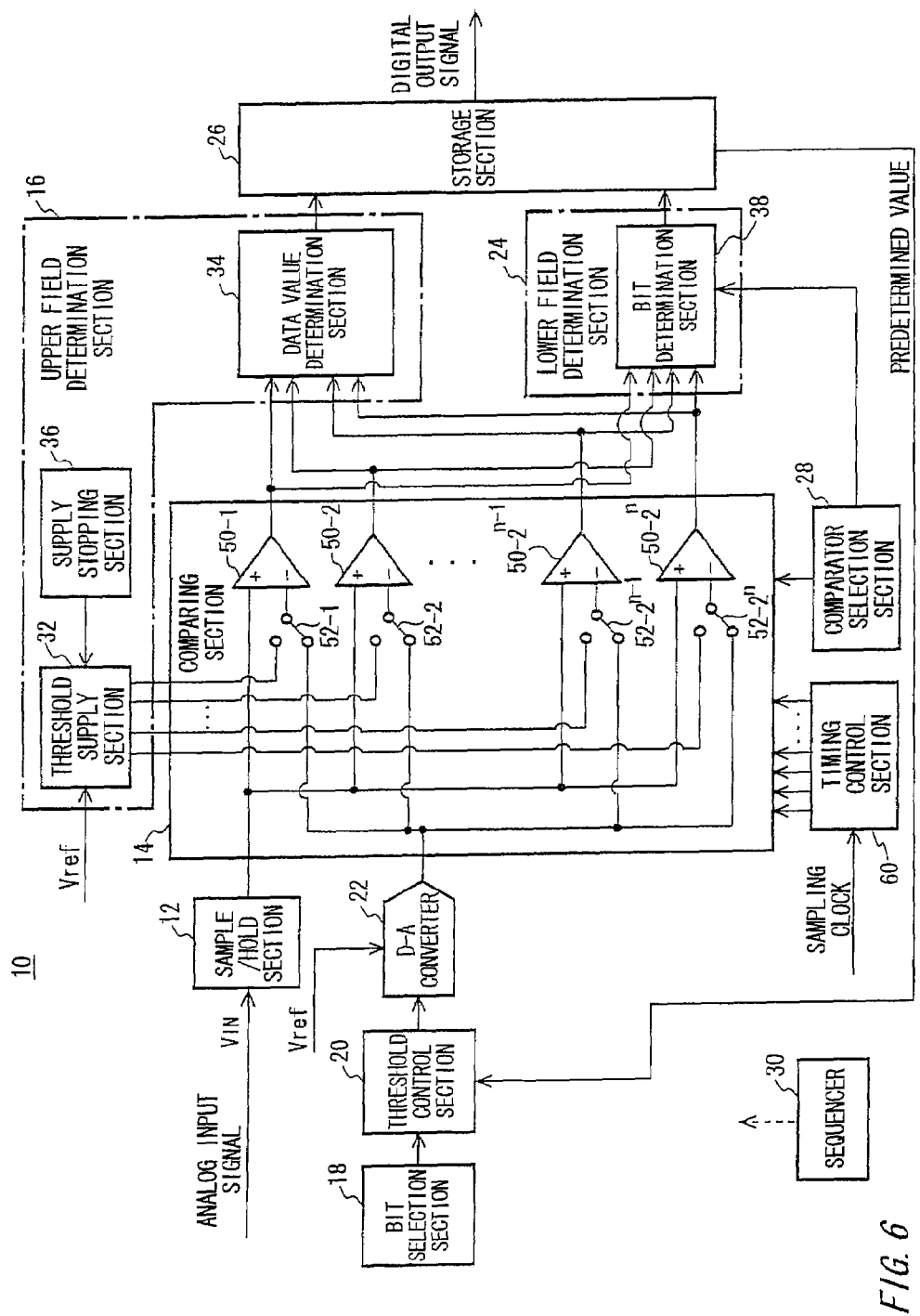
FIG. 6 shows a configuration of the A-D converter 10 according to a second aspect of an embodiment of the present invention.

FIG. 6 shows a configuration of the A-D converter 10 according to a second aspect of the present invention. The A-D converter 10 according to the second aspect adopts generally the same structure and function as the A-D converter 10 according to the present embodiment shown in FIG. 1, and therefore identical parts having a structure and function generally the same as that of the parts shown in FIG. 1 are given the same numbering and the following description omits identical points.

The A-D converter 10 according to the second aspect is further provided with a timing control section 60. During the lower determination phase, the timing control section 60 supplies a strobe signal to each of the plurality of comparators 50 (there are $2^n$ comparators 50 in the second aspect) and also controls timing of the comparison between the analog input signal and the analog threshold value performed by each of the plurality of comparators 50.

Specifically, during the lower determination phase, the timing control section 60 makes the first comparator 50-1 from among the plurality of comparators 50 perform the comparison at a first comparison time during the conversion time for determining the values of the conversion target bits. The timing control section 60 then makes the second comparator 50-2 from among the plurality of comparators 50 perform the comparison at a second comparison time, which is different from the first comparison time, during the conversion time for determining the values of the conversion target bits. Therefore, through the timing control section 60, more precise A-D conversion can be achieved because an effect of errors made by the comparator 50 due to momentary noise is decreased.

For example, the timing control section 60 may generate a first strobe signal designating a first comparison time and a second strobe signal designating a second comparison time by delaying the sampling clock, which determines the conversion time of a one-bit unit, using a delay element having a delay amount less than one cycle of the sampling clock. In such a case, the first comparator 50-1 compares the analog input signal and the analog threshold based on the first strobe signal and the second comparator 50-2 compares the analog input signal and the analog threshold based on the second strobe signal. Therefore, through the timing control section 60, a plurality of strobe signals can be generated having timing intervals therebetween that are less than or equal to a cycle of the sampling clock which determines the conversion time of a one-bit unit.

In the second aspect, during the lower determination phase, the timing control section 60 supplies in parallel to the $2^n$ comparators 50 the first through ($2^n$)-th strobe signals, which have a relative timing that is out of alignment with each other by a degree of time less than or equal to a cycle of the sampling clock. Furthermore, during the lower determination phase in the second aspect, the timing control section 60 supplies to the $2^n$ comparators 50 the common strobe signals designating generally the same comparison time.

Figure 7:
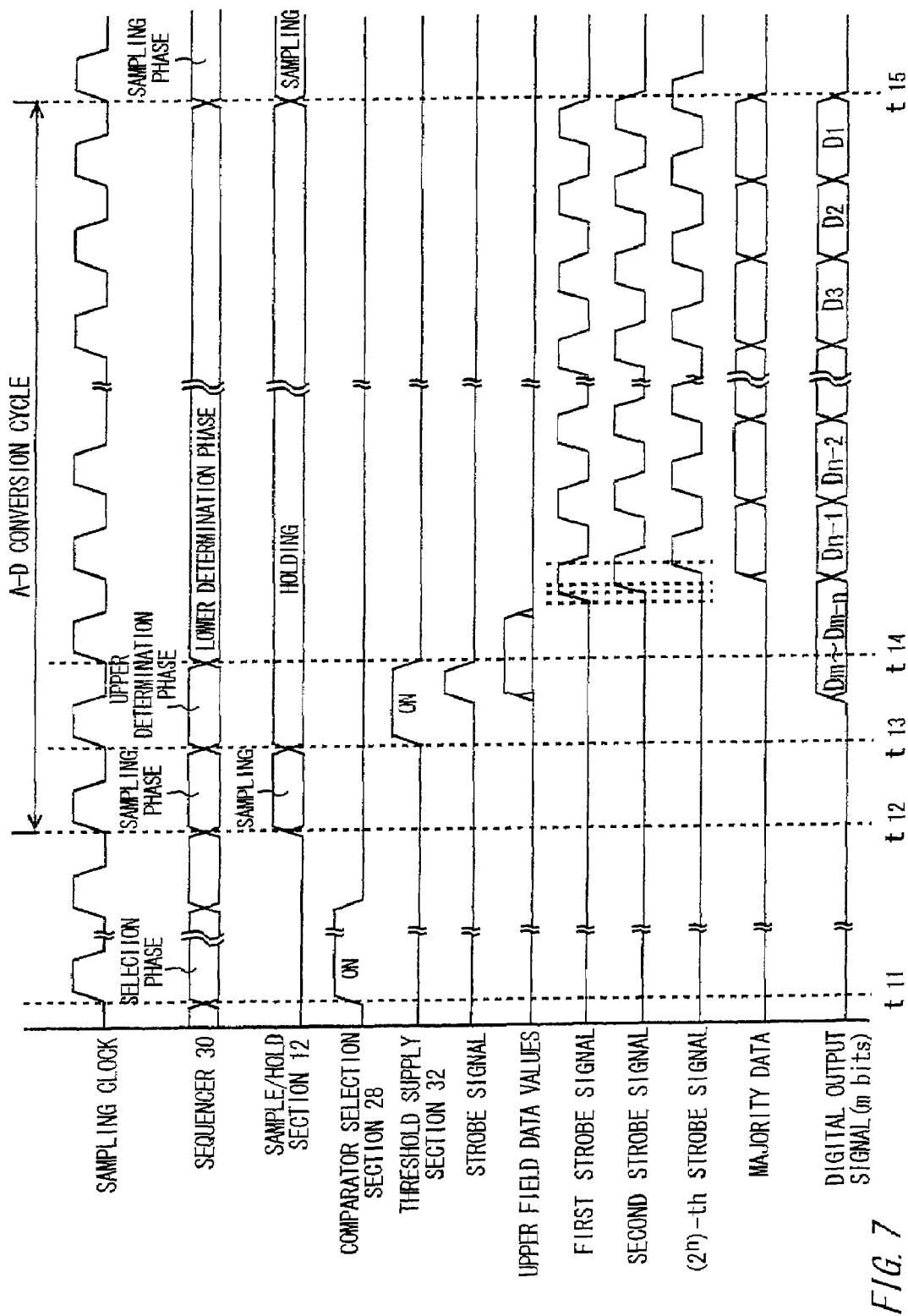
FIG. 7 shows an example timing chart of the analog to digital conversion process by the A-D converter 10 according to the second aspect.

FIG. 7 shows an example timing chart of the analog to digital conversion process by the A-D converter 10 according to the second aspect. After the analog threshold values, which are D-A converted threshold value data, are provided to the each of the $2^n$ comparators 50 during selection of each conversion target bit in the lower determination phase, the sequencer 30 instructs the timing control section 60 to supply the strobe signals (t14 to t15). Upon receiving the supply instruction, the timing control section 60 supplies in parallel from the sequencer 30 to the $2^n$ comparators 50 the first through ($2^n$)-th strobe signals, which have a relative timing that is out of alignment with each other by a degree of time less than or equal to a cycle of the sampling clock. In such a case, the timing control section 60 may supply the strobe signals to the k comparators 50 selected by the comparator selection section 28.

Then, at a time designated by the corresponding strobe signal, each of the $2^n$ comparators 50 compare the analog input signal held by the sample/hold unit 12 to the analog threshold value supplied from the D-A conversion section 22. The bit determination unit 38 then determines the values (zero or one) of the conversion target bits by making a determination based on, for example, a majority of the comparison results of the k comparators 50 selected by the comparator selection section 28.

Figure 8:
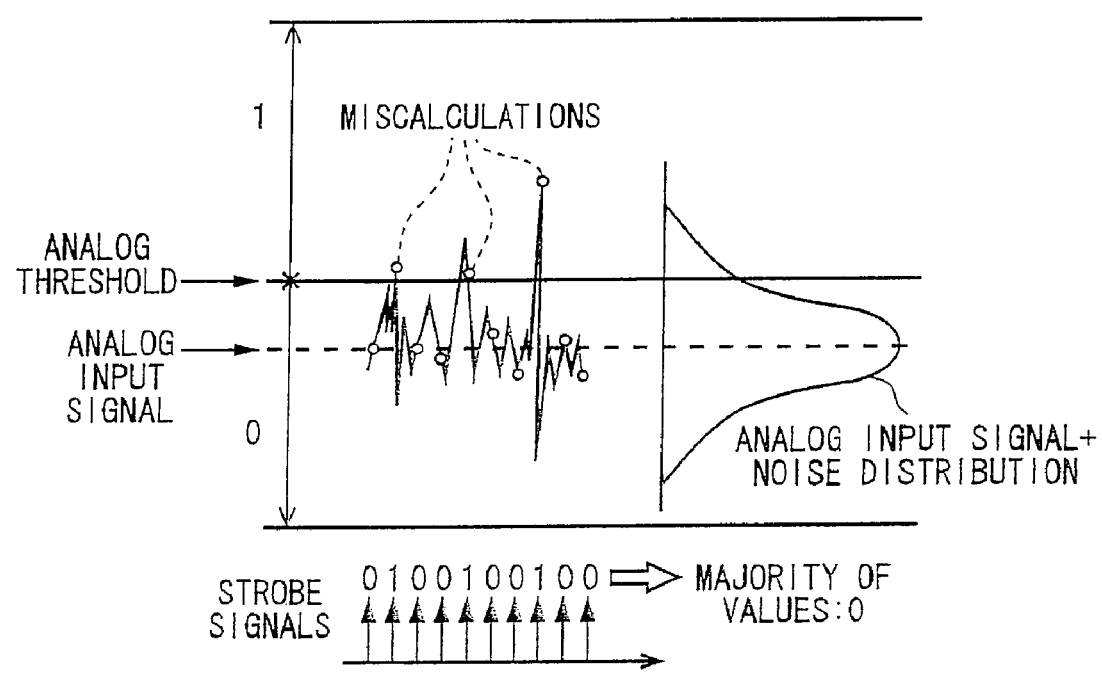
FIG. 8 shows an example of a plurality of comparison times and a distribution of noise and the analog input signal input into the comparing section 14 according to the second aspect.
Figure 9:
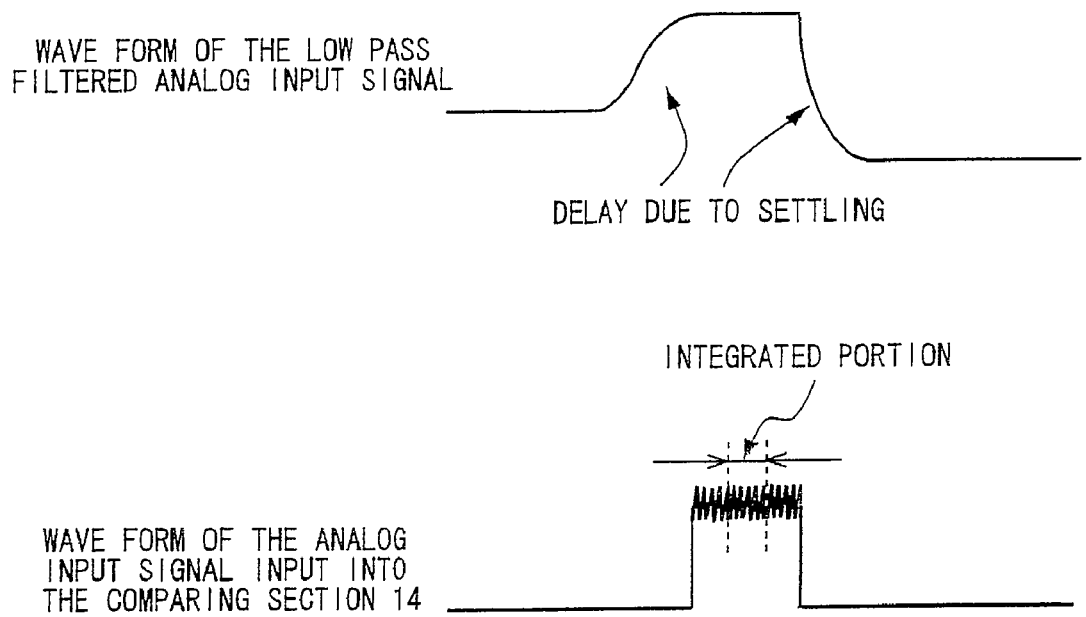
FIG. 9 shows an example of a wave-form of a low pass filtered analog input signal and an analog input signal that is not low pass filtered input into the comparing section 14 of the second aspect.

FIG. 8 shows an example of a plurality of comparison times and a distribution of noise and the analog input signal input into the comparing section 14 according to the second aspect. FIG. 9 shows an example of a wave-form of a low pass filtered analog input signal and an analog input signal that is not low pass filtered input into the comparing section 14 of the second aspect.

As shown in FIG. 8, there is a case where the analog input signal input into the A-D converter 10 includes thermal noise in a Gaussian distribution. In a case where this thermal noise is included, there is a rare occurrence that a large amount of noise is superimposed on the analog input signal. In a case where the large amount of noise is generated at a time designated by the strobe signal, there is a possibility that the comparing section 14 outputs an incorrect comparison result. Because the successive approximation type A-D converter determines the values sequentially from the highest bit, a miscalculation of the highest bit results in the output of data values including a large error.

To solve the aforementioned problem, low pass filtering of the analog input signal has been considered. However, as shown in FIG. 9, the low pass filtered analog input signal is delayed by settling, which results in a longer conversion time.

Correct comparison results can be achieved through the A-D converter 10 according to the second embodiment, if the effect of a momentary large amount of noise that occurs infrequently is ignored, because the determination is made based on a majority of the plurality of comparison results having different timing. Furthermore, as shown in FIG. 9, a result in which the integrated wave-form of the analog input signal is equal to the A-D converted data values can be achieved through the A-D converter 10 without delaying the analog input signal. In the manner described above, through the A-D converter 10 according to the second aspect, A-D conversion having a short conversion time and high precision can be realized.

During the lower determination phase, the timing control section 60 of the A-D converter 10 according to the second aspect may change the delay time of the strobe signals supplied to the plurality of comparators 50 in accordance with random numbers. Therefore, through the timing control section 60, the effect of miscalculations caused by periodic noise can be avoided, even in a case where periodic noise generated in the same cycle of the sampling clock is included.

Figure 10:
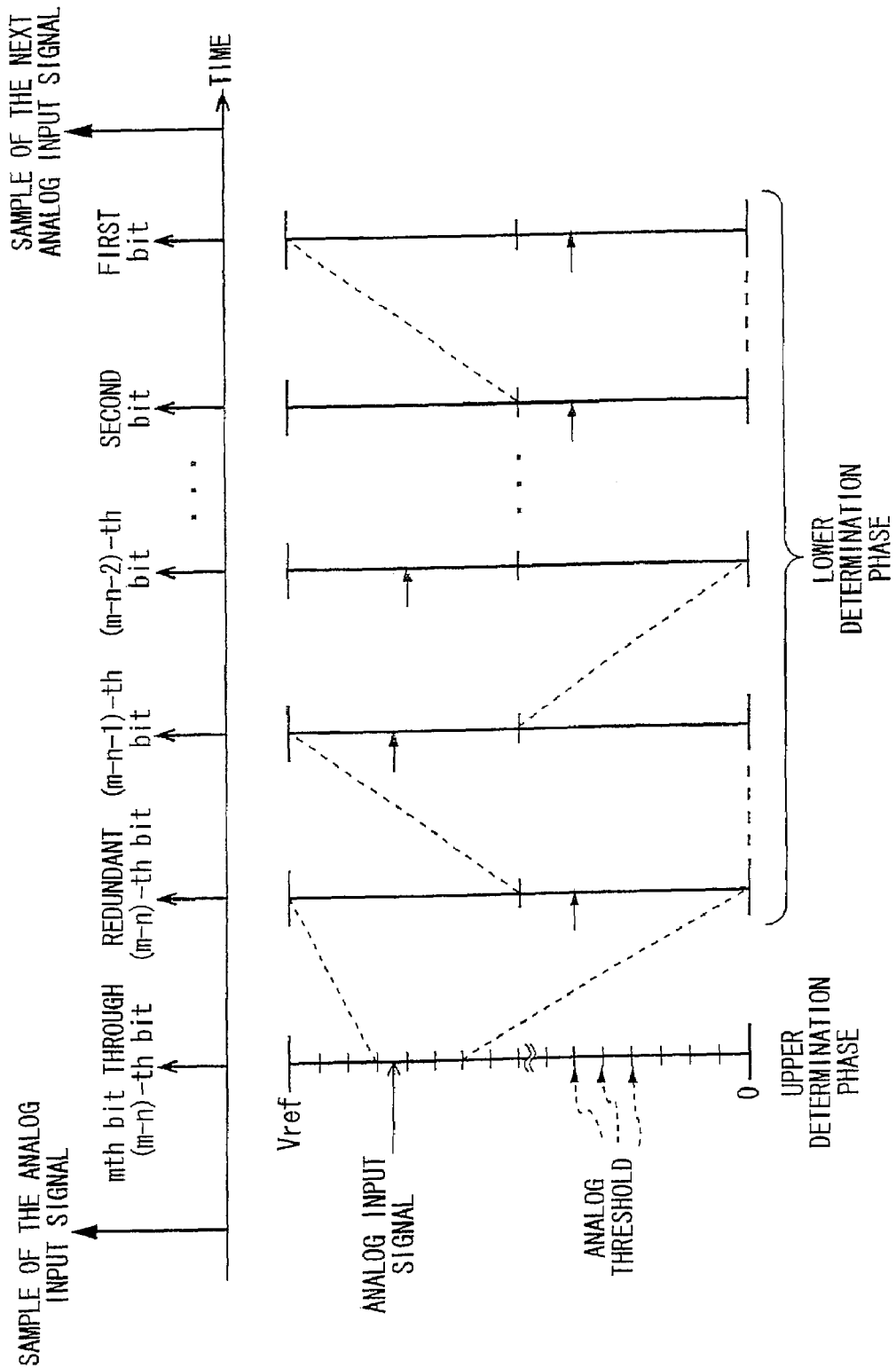
FIG. 10 shows an example of an over range comparison process by the A-D converter 10 according to a third aspect of an embodiment of the present invention.

FIG. 10 shows an example of an over range comparison process by the A-D converter 10 according to a third aspect of the present embodiment. The A-D converter 10 according to the third aspect adopts generally the same structure and function as the A-D converter 10 according to the present embodiment shown in FIG. 1, and therefore the following description omits identical points.

The lower field determination section 24 according to the third aspect executes the over range comparison process. In other words, in the third aspect, a bit that is a prescribed number of bits from the bottom of the upper field is overlapped with a bit that is a prescribed number of bits from the top of the lower field.

For example, as shown in FIG. 10, during the upper determination phase, the upper field determination section 16 determines the data values from the highest bit (the m-th bit) to the (m-n)-th bit within the upper field of the digital output signal. In such a case the lower field determination section 24 may determine, for example, the lower field data values from the (m-n)-th bit (or any arbitrary bit higher than the (m-n)-th bit) to the lowest bit (the first bit) in the digital output signal during the lower determination phase.

In such a manner, the A-D converter 10 according to the third aspect determines the values of the lower bits of the upper field during both the upper determination phase and the lower determination phase. In a case where the value of the (m-n)-th bit determined during the upper determination phase and the value of the (m-n)-th bit determined during the lower determination phase are different, the storage section 26 outputs the value of the (m-n)-th bit determined during the lower determination phase. Accordingly, the lower field determination section 24 can correct an error occurring during the upper determination phase during the lower determination phase. Therefore, through the A-D converter 10 according to the third aspect, more precise A-D conversion can be achieved.

Figure 11:
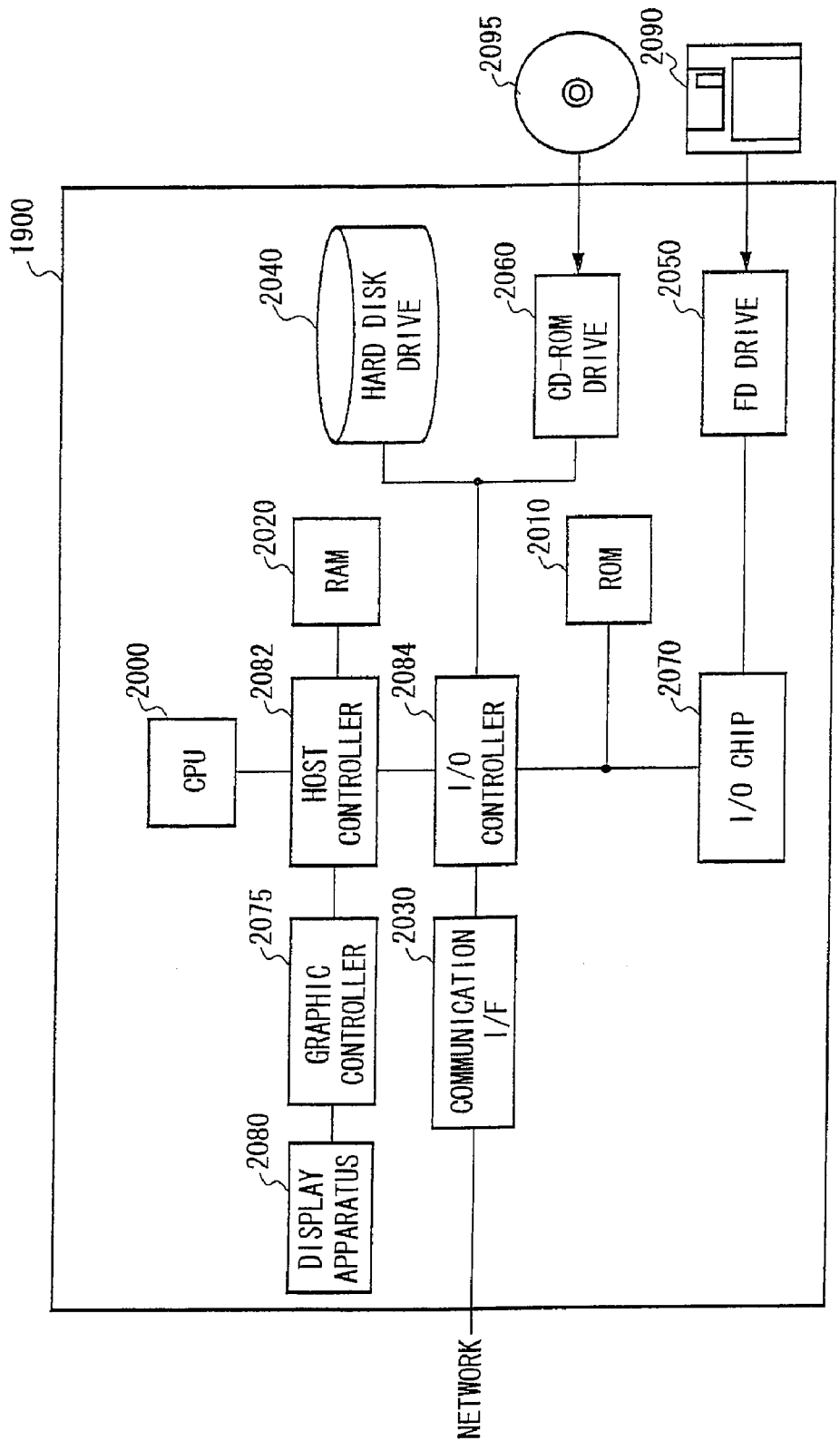
FIG. 11 shows an example of a hardware configuration of a computer 1900 according to an embodiment of the present invention.

FIG. 11 shows an example of a hardware configuration of a computer 1900 according to the present embodiment. The computer 1900 according to the present embodiment is provided with a CPU peripheral including a CPU 2000, a RAM 2020, a graphic controller 2075, and a displaying apparatus 2080, all of which are connected to each other by a host controller 2082; an input/output section including a communication interface 2030, a hard disk drive 2040, and a CD-ROM drive 2060, all of which are connected to the host controller 2082 by an input/output controller 2084; and a legacy input/output section including a ROM 2010, a flexible disk drive 2050, and an input/output chip 2070, all of which are connected to the input/output controller 2084.

The host controller 2082 is connected to the RAM 2020 and is also connected to the CPU 2000 and graphic controller 2075 accessing the RAM 2020 at a high transfer rate. The CPU 2000 operates to control each section based on programs stored in the ROM 2010 and the RAM 2020. The graphic controller 2075 acquires image data generated by the CPU 2000 or the like on a frame buffer disposed inside the RAM 2020 and displays the image data in the displaying apparatus 2080. In addition, the graphic controller 2075 may internally include the frame buffer storing the image data generated by the CPU 2000 or the like.

The input/output controller 2084 connects the communication interface 2030 serving as a relatively high speed input/output apparatus, the hard disk drive 2040, and the CD-ROM drive 2060 to the host controller 2082. The communication interface 2030 communicates with other apparatuses via a network. The hard disk drive 2040 stores the programs and data used by the CPU 2000 housed in the computer 1900. The CD-ROM drive 2060 reads the programs and data from a CD-ROM 2095 and provides the read information to the hard disk drive 2040 via the RAM 2020.

Furthermore, the input/output controller 2084 is connected to the ROM 2010, and is also connected to the flexible disk drive 2050 and the input/output chip 2070 serving as a relatively high speed input/output apparatus. The ROM 2010 stores a boot program performed when the computer 1900 starts up, a program relying on the hardware of the computer 1900, and the like. The flexible disk drive 2050 reads programs or data from a flexible disk 2090 and supplies the read information to the hard disk drive 2040 via the RAM 2020. The input/output chip 2070 connects the flexible disk drive 2050 to each of the input/output apparatuses via, for example, a parallel port, a serial port, a keyboard port, a mouse port, or the like.

The programs provided to the hard disk drive 2040 via the RAM 2020 are stored in a storage medium, such as the flexible disk 2090, the CD-ROM 2095, or an IC card, and provided by a user. The programs are read from storage medium, installed in the hard disk drive 2040 inside the computer 1900 via the RAM 2020, and performed by the CPU 2000.

The programs installed in the computer 1900 to make the computer 1900 function as a control apparatus of the A-D converter 10 are provided with a lower field determination module, a bit selection module, a threshold control module, a lower field determination module, a storage module, a comparator selection module, and a sequencer module. These programs and modules prompt the CPU 2000 or the like to make the computer 1900 function as the upper field determination section 16, the bit selection section 18, the threshold control section 20, the lower field determination section 24, the storage section 26, the comparator selection section 28, and the sequencer 30, respectively.

The programs and modules shown above may also be stored in an external storage medium. The flexible disk 2090, the CD-ROM 2095, an optical storage medium such as a DVD or CD, a magneto-optical storage medium, a tape medium, a semiconductor memory such as an IC card, or the like can be used as the storage medium. Furthermore, a storage apparatus such as a hard disk or RAM that is provided with a server system connected to the Internet or a specialized communication network may be used to provide the programs to the computer 1900 via the network.

While an aspect of the present invention has been described based on an embodiment, the technical scope of the invention is not limited to the above described embodiment. It is apparent to persons skilled in the art that various alternations and improvements can be added to the above-described embodiment. It is also apparent from the scope of the claims that the embodiments added with such alternations or improvements can be included in the technical scope of the invention.

What is claimed is:

1. An A-D converter outputting a digital output signal which is a digitalized analog input signal, comprising:
   a plurality of comparators, each of which compares the analog input signal to analog threshold values;
   an upper field determination section which, during an upper determination phase, supplies in parallel to each of the plurality of comparators the plurality of analog threshold values expressing boundaries of ranges corresponding to each data value acquired from an upper field of a number of bits previously designated in the digital output signal, detects whether the analog input signal is associated with one of the ranges based on comparison results by the plurality of comparators, and narrows down the data values of the upper field to data values corresponding to a range between a largest of the analog threshold values less than or equal to the analog input signal and a smallest of the analog threshold values greater than or equal to the analog input signal;
   a bit selection section which, during a lower determination phase, selects conversion target bits sequentially from a highest bit to a lowest bit within a lower field, while ignoring the upper field in the digital output signal;
   a threshold control section which, during the lower determination phase, determines threshold data values expressing boundary values of zero and one of the conversion target bits based on a predetermined value of a bit higher than the conversion target bits;
   a D-A conversion section which, during the lower determination phase, supplies to each of the plurality of comparators the analog threshold values which are the D-A converted threshold data; and
   a lower field determination section which, during the lower determination phase, determines values of the conversion target bits based on a plurality of comparison results of the plurality of comparators.

2. The A-D converter according to claim 1, wherein the lower field determination section determines values of the conversion target bits based on a majority of the plurality of comparison results.

3. The A-D converter according to claim 1, further comprising a comparator selection section, wherein:
   the comparator selection section measures a margin of error for each of the plurality of comparators by connecting a reference potential to an input terminal of each comparator, changing a potential of another input terminal, and measuring a difference between the reference potential and the potential reflecting the comparison result, and then selects the comparators having small margins of error from among the plurality of comparators based on the measurement result; and
   the lower field determination section determines values of the conversion target bits based on comparison results of the plurality of comparators selected by the comparator selection section.

4. The A-D converter according to claim 1, further comprising a timing control section controlling timing of the comparisons between the analog input signal and the analog threshold values made by each of the plurality of comparators during the lower determination phase, wherein the timing control section makes a first comparator from among the plurality of comparators perform the comparison at a first comparison time during a conversion period determining values of the conversion target bits and makes a second comparator from among the plurality of comparators perform the comparison at a second comparison time different from the first time during this conversion period.

5. The A-D converter according to claim 4, wherein:
   the timing control section generates a first strobe signal designating the first comparison time and a second strobe signal designating the second comparison time by delaying a sampling clock determining a conversion time of a one-bit unit by using a delay element having a delay amount less than one cycle of the sampling clock;
   the first comparator compares the analog input signal to the analog threshold values based on the first strobe signal; and
   the second comparator compares the analog input signal to the analog threshold values based on the second strobe signal.

6. The A-D converter according to claim 1, wherein the upper field determination section includes:
   a threshold supply section supplying in parallel to each of the plurality of comparators the plurality of analog threshold values expressing boundaries of a range corresponding to each data value acquired from the upper field; and
   a supply stopping section stopping a supply of the analog threshold values from the threshold supply section to the plurality of comparators during phases other than the upper determination phase.

7. The A-D converter according to claim 1, wherein a bit which is a prescribed number of bits from a bottom of the upper field is overlapped with a bit which is a prescribed number of bits from a top of the lower field.

8. An A-D conversion method performed by an A-D converter outputting a digital output signal which is a digitalized analog input signal, wherein the A-D converter includes a plurality of comparators, each of which compares the analog input signal to analog threshold values, the A-D conversion method comprising:

during an upper determination phase, supplying in parallel to each of the plurality of comparators the plurality of analog threshold values expressing boundaries of ranges corresponding to each data value acquired from an upper field of a number of bits previously designated in the digital output signal, detects whether the analog input signal is associated with one of the ranges based on comparison results by the plurality of comparators, and narrows down the data values of the upper field to data values corresponding to a range between a largest of the analog threshold values less than or equal to the analog input signal and a smallest of the analog threshold values greater than or equal to the analog input signal;

during a lower determination phase, selecting conversion target bits sequentially from a highest bit to a lowest bit within a lower field, while ignoring the upper field in the digital output signal;

during the lower determination phase, determining threshold data values expressing boundary values of zero and one of the conversion target bits based on a predetermined value of a bit higher than the conversion target bits;

during the lower determination phase, supplying to each of the plurality of comparators the analog threshold values which are the D-A converted threshold data; and during the lower determination phase, determining values of the conversion target bits based on a plurality of comparison results of the plurality of comparators.

* * * * *